(12) United States Patent
Gurr (10) Patent No.: US 10,792,521 B2
(45) Date of Patent: Oct. 6, 2020

(54) CONTROLLER FOR, AND METHOD OF, CONTROLLING A BREATHING APPARATUS

(71) Applicant: Avon Polymer Products Limited, Melksham, Wiltshire (GB)

(72) Inventor: Kevin Peter Gurr, Poole (GB)

(73) Assignee: AVON POLYMER PRODUCTS LIMITED, Melksham, Wiltshire (GB)

(*) Notice: Subject to any disclaimer, the term of this patent is extended or adjusted under 35 U.S.C. 154(b) by 1017 days.

(21) Appl. No.: 15/128,167

(22) PCT Filed: Mar. 12, 2015

(86) PCT No.: PCT/GB2015/050719
§ 371 (c)(1),
(2) Date: Sep. 22, 2016

(87) PCT Pub. No.: WO2015/145106
PCT Pub. Date: Oct. 1, 2015

(65) Prior Publication Data
US 2017/0100610 A1 Apr. 13, 2017

(30) Foreign Application Priority Data
Mar. 27, 2014 (GB) .................................. 1405548.7

(51) Int. Cl.
*A62B 9/00* (2006.01)
*A62B 7/02* (2006.01)
(Continued)

(52) U.S. Cl.
CPC ................ *A62B 9/006* (2013.01); *A62B 7/02* (2013.01); *B63C 11/24* (2013.01); *A61M 2016/1025* (2013.01)

(58) Field of Classification Search
CPC ........... A62B 7/02; A62B 9/006; B63C 11/24; A61M 2016/1025
See application file for complete search history.

(56) References Cited

U.S. PATENT DOCUMENTS 3,556,098 A * 1/1971 Kanwisher ........ A61M 16/0051
128/202.22
6,712,071 B1 * 3/2004 Parker ..................... A62B 7/02
128/201.25
(Continued)

FOREIGN PATENT DOCUMENTS

GB 2201602 A 9/1988
WO WO 2009/058081 A1 5/2009

OTHER PUBLICATIONS

Search Report and Written Opinion in corresponding GB Application No. 1504164.3, dated Sep. 3, 2015.

*Primary Examiner* — Bradley H Philips
(74) *Attorney, Agent, or Firm* — Leason Ellis LLP (57) ABSTRACT

A controller for controlling a breathing apparatus that comprises a plurality of oxygen sensors, each for sensing an oxygen content of a gas in the breathing apparatus, the controller being configured to control the operation of the breathing apparatus based on the output of one or more of the oxygen sensors and additional information relating to the operation of the breathing apparatus. Also a breathing apparatus comprising the controller and the plurality of oxygen sensors.

17 Claims, 1 Drawing Sheet

(51) Int. Cl.
  *B63C 11/24* (2006.01)
  *A61M 16/10* (2006.01)

(56) References Cited

U.S. PATENT DOCUMENTS

| | | | |
|---|---|---|---|
| 7,353,824 B1 | 4/2008 | Forsyth et al. | |
| 2005/0061318 A1* | 3/2005 | Faram | A61M 16/0096 128/204.18 |
| 2007/0215157 A1 | 9/2007 | Straw | |
| 2010/0313887 A1 | 12/2010 | Sieber | |
| 2011/0041848 A1* | 2/2011 | Stone | A61M 16/12 128/203.14 |
| 2012/0055815 A1* | 3/2012 | Truex | A62B 9/006 206/205 |
| 2013/0066564 A1* | 3/2013 | Forsyth | G01N 21/274 702/24 |

\* cited by examiner

CONTROLLER FOR, AND METHOD OF, CONTROLLING A BREATHING APPARATUS

CROSS-REFERENCE TO RELATED APPLICATIONS

This application is a U.S. National Stage Application under 35 U.S.C. § 371 of International Patent Application No. PCT/GB2015/050719, filed Mar. 12, 2015 which claims priority to GB Application No. 1405548.7, filed Mar. 27, 2014, which are hereby incorporated by reference in their respective entireties.

BACKGROUND OF THE INVENTION

Field of the Invention

The present invention relates to a controller for controlling a breathing apparatus.

The present invention also relates to a method of controlling a breathing apparatus.

Summary of the Prior Art

A rebreather is a type of breathing apparatus in which the used gas exhaled by a user of the breathing apparatus is recirculated and reused, to permit the rebreathing (recycling) of the unused oxygen content of the used gas. Used gas has a lower oxygen content than unused gas, because some of the oxygen in the unused gas is used (metabolised) by the user of the breathing apparatus. Oxygen is therefore normally added to the used gas to replace the oxygen used by the user of the breathing apparatus.

It is important to control the oxygen content of the gas in the rebreather. In particular, it is important to control the concentration (or the proportion) of oxygen in the gas in the rebreather, which is normally expressed by the partial pressure of oxygen in the gas in the rebreather. The partial pressure of oxygen ($PPO_2$) in a gas mixture is given by:

$$PPO_2 = P \times FO_2 \quad (1)$$

where P is the total pressure of the gas mixture and $FO_2$ is the volume fraction of oxygen in the gas mixture.

If the partial pressure of oxygen in the gas in the rebreather falls below a minimum safe partial pressure (which may depend on e.g. the user's physiology and level of exertion and on the exposure time), the user of the breathing apparatus may be at risk of unconsciousness or death due to hypoxia. On the other hand, if the partial pressure of oxygen in the gas in the rebreather rises above a maximum safe partial pressure (which may also depend on e.g. the user's physiology and level of exertion and on the exposure time), the user of the breathing apparatus may be at risk of oxygen toxicity, which may result in seizures and even death in severe cases.

Therefore, it is important to control the partial pressure of oxygen in the gas in the rebreather, so that the partial pressure of oxygen remains within safe limits. In known rebreathers, this is achieved by providing the rebreather with a plurality of oxygen sensors for sensing the partial pressure of oxygen in the gas in the rebreather, and a control system for controlling the partial pressure of oxygen in the gas in the rebreather (e.g. to be equal to a target partial pressure of oxygen, which may be referred to as the target set-point of the rebreather) based on the output of one or more of the plurality of oxygen sensors.

Oxygen sensors used in breathing apparatus such as rebreathers may comprise a cell, for example an electro-galvanic fuel cell, and an electronics package. When the oxygen sensor comes into contact with oxygen, in the case of the electro-galvanic fuel cell, a chemical reaction occurs in the electro-galvanic fuel cell that leads to the generation of an electrical current in the electro-galvanic fuel cell.

In some oxygen sensors that comprise an electro-galvanic fuel cell, the electro-galvanic fuel cell may comprise a lead (Pb) anode, a platinum (Pt) cathode and a potassium hydroxide (KOH) electrolyte (of course, alternative materials may be, and are, used instead of these specific materials in other types of oxygen sensor). When such an electro-galvanic fuel cell comes into contact with oxygen, oxygen in contact with the cathode is reduced to hydroxyl ions, with a balancing reaction of lead oxidation at the anode. The reaction equations for such an electro-galvanic fuel cell are:

Cathode: $O_2 + 2H_2O + 4e^- \rightarrow 4OH^-$

Anode: $2Pb + 4OH^- \rightarrow 2PbO + 2H_2O + 4e^-$

Overall: $O_2 + 2Pb \rightarrow 2PbO \quad (2)$

The result of these reactions is that the electro-galvanic fuel cell generates an electrical current that is proportional to the rate of oxygen consumption by the electro-galvanic fuel cell. This current may be measured by placing a load resistor between the cathode and the anode and measuring the resultant voltage drop across the resistor. Other types of cell may function in a similar manner, i.e. they may generate an electrical current that is proportional to a rate of oxygen consumption by the cell, or to the magnitude of the oxygen content being sensed by the oxygen sensor.

As shown in equation (2), during the electro-chemical reaction the oxygen converts lead in the anode to lead oxide, thereby generating the electrical current produced by the electro-galvanic fuel cell. Since pure lead in the anode is used up during the electrochemical reaction, the amount and surface area of pure lead in the anode reduces over time. This reduction causes the maximum electrical output of the electro-galvanic fuel cell to reduce (decay) over time. This is because the size and surface area of the anode control the internal impedance of the electro-galvanic fuel cell, and as the anode is consumed, and the amount and surface area of lead in the anode decreases, the internal impedance of the electro-galvanic fuel cell increases, thereby reducing the maximum amount of current that the sensor can supply (and consequently the maximum voltage that can be measured across the internal load resistor). Eventually, if all of the lead in the anode were oxidised, the maximum electrical output of the electro-galvanic fuel cell would fall to zero. Similar problems occur in electro-galvanic fuel cells comprising different materials. Similar problems may also occur in oxygen sensors having different types of cell, e.g. the maximum output of the cell may reduce with continued operation of the cell.

The maximum $PPO_2$ that an oxygen sensor is capable of measuring depends on the maximum current that the oxygen sensor can supply. Therefore, as the maximum electrical output of the electro-galvanic fuel cell reduces (decays) with age, the maximum $PPO_2$ that the oxygen sensor is capable of measuring also reduces with age. Assuming that a new oxygen sensor is capable of measuring a $PPO_2$ limit of 3.5 atm when it is installed in a rebreather, as the oxygen sensor ages the maximum current that it can supply will reduce (as discussed above), and the same oxygen sensor after a year may only be able to indicate a $PPO_2$ of 1.5 atm.

This effect may be referred to as "current limiting" of the oxygen sensor. Where the $PPO_2$ being measured is greater than a $PPO_2$ corresponding to the maximum current that the oxygen sensor can supply, the oxygen sensor may supply this maximum current. The oxygen sensor may therefore indicate the $PPO_2$ corresponding to the maximum current, which is less than the actual $PPO_2$ being measured. The oxygen sensor may therefore give an incorrect $PPO_2$ reading for partial pressures above a particular partial pressure (a partial pressure corresponding to a maximum current that the oxygen sensor can generate). Similar problems may also occur in oxygen sensors having different types of cell, e.g. as the oxygen sensor ages the maximum output of the cell may decrease, and the cell may therefore output the maximum output for oxygen contents above a particular oxygen content (the magnitude of which decreases with age of the oxygen sensor).

As such, an oxygen sensor may correctly indicate a $PPO_2$ of e.g. 1.0 atm when exposed to a $PPO_2$ of 1.0 atm, but may only be able to supply sufficient current to indicate a $PPO_2$ of e.g. 1.2 atm when exposed to a higher $PPO_2$ of e.g. 1.3 atm while diving. Not only may the user of the breathing apparatus be unaware of this incorrect reading by the oxygen sensor, but if the limited cell output is below the $PPO_2$ target set-point of the rebreather (the target $PPO_2$ that the rebreather is configured to maintain in the gas in the rebreather), the rebreather may also continue to add oxygen to the gas in the rebreather even though the $PPO_2$ in the rebreather is rising to dangerously high levels. As discussed below, rebreather designs and diving procedures have been developed to try to minimise the risk of such events. A newly manufactured sensor will also be current limited for the same reasons, and typically will limit around 175 mV or (assuming 10 mv is 0.21 atm) 3.675 atm.

As discussed above, the time taken for the output of the electro-galvanic fuel cell to decay by a given amount is primarily a function of the amount of oxygen that the oxygen sensor is exposed to. Since the oxygen sensor's aging process is primarily a function of the $PPO_2$ it is subjected to (a higher $PPO_2$ oxidises the lead in the anode more quickly), a sensor left in 100% oxygen will have a shorter life span than one left in 21% oxygen. The normal expected life of an oxygen sensor which would be used in a rebreather (a fast reacting sensor) is about 30 weeks in 100% oxygen at the surface (1.0 atm). Use in a rebreather environment will reduce this life span, but by how much is difficult to estimate.

These effects are somewhat mitigated in known oxygen sensors used in rebreathers by forming the anode from a collection of small balls of lead compressed into a doughnut shape. This configuration of the anode has the effect of evening out the usage of lead throughout the life of the oxygen sensor, and therefore helps to reduce the effects of the usage of lead in the anode. Therefore, this configuration may help to maintain a fairly constant output of the oxygen sensor as the lead in the anode is used up.

However, since the output of the oxygen sensor remains nearly constant until most of the lead in the anode has been oxidised, the oxygen sensor's 'end of life' (i.e. the time at which substantially all of the lead in the anode has been oxidised) is difficult to predict. This unpredictability is disadvantageous, since it means that an oxygen sensor may fail (or become current limited) unexpectedly and with little warning. In addition, although the oxygen sensor exhibits a measurable decrease in output until the end of its operational life, this is not a continuous linear reduction, and therefore it may be difficult to predict when the oxygen sensor will become significantly current limited. Similar problems may occur with other configurations of oxygen sensor, for example oxygen sensors comprising different materials or with a different configuration of the anode or with a different type of cell (i.e. a type of cell other than an electro-galvanic fuel cell).

One way to test for current limiting of an oxygen sensor is to elevate the $PPO_2$ (for example to above 1.0 atm, and preferably to the required operating $PPO_2$ of the rebreather) to determine if the output of the oxygen sensor becomes static above a particular $PPO_2$. This may be achieved by submerging the rebreather and performing a 100% oxygen flush of the rebreather at a safe depth (e.g. a maximum depth of 6 m). If the $PPO_2$ stabilises at or near a predetermined value (e.g. 1.6 atm (±0.1 atm)), there may be reasonable confidence that current limiting will not occur during the dive, providing that the sensors are not adversely affected by moisture or temperature during the dive. A Diluent flush at depth, where the Diluent $PPO_2$ is also above the rebreather's set-point, may also provide the same confirmation.

In summary, oxygen sensors are relatively linear in their response to increasing $PPO_2$ (in a stable environment). This linearity has an upper limit (of $PPO_2$) after which they become non-linear, or static. As the sensor ages this upper limit reduces. For example, a sensor that was linear to 3.0 atm may, with time, only be linear to 2.0 atm.

Commercially available rebreathers have two main components for controlling the $PPO_2$ in the gas in the rebreather: the oxygen sensors (commonly three oxygen sensors) and a $PPO_2$ control system. The $PPO_2$ control system generally comprises an amplifier system to interface the oxygen sensors to the control electronics and an electronic "voting logic" system that determines how to combine the outputs of the different oxygen sensors to determine the $PPO_2$ in the gas in the rebreather.

The simplest way of determining the $PPO_2$ in the gas in the breathing apparatus is to average the sensor outputs of the plurality of oxygen sensors, e.g. by adding the sensor outputs of the plurality of oxygen sensors together and then dividing the total by the number of oxygen sensors.

The function of the electronic "voting logic" system is to determine how to combine the outputs of the oxygen sensors to determine the $PPO_2$ in the gas in the rebreather. For example, where one of the oxygen sensors is not functioning correctly (e.g. it is current limited, incorrectly calibrated, or faulty, causing it to provide an incorrect sensor output), ideally the sensor output of that oxygen sensor should be disregarded when determining the $PPO_2$ in the gas in the rebreather. Otherwise, the $PPO_2$ may be incorrectly determined.

As discussed in detail above, there are failure modes for oxygen sensors used in rebreathers that can mean that the $PPO_2$ reading from the oxygen sensor becomes near static even though the $PPO_2$ in the gas in the rebreather is rising (i.e. the sensor may be current-limited at a current corresponding to a partial pressure below the partial pressure being measured). This can be potentially hazardous to the diver, because if the control system merely averages the outputs of all of the oxygen sensors, the control system may determine that the $PPO_2$ in the gas in the rebreather is below the target set-point value, when actually the $PPO_2$ in the gas in the rebreather is at, or above, the target set-point value. The control system may therefore continue to inject oxygen into the gas in the rebreather when further injection of oxygen is unnecessary, so that a potentially hazardous $PPO_2$ is reached.

In order to try to avoid problems of this kind, in known electronic "voting logic" systems predetermined criteria are used to determine which oxygen sensor outputs should be used when determining the $PPO_2$ in the gas in the rebreather, and which (if any) should be disregarded. An example of a simple voting system typically used in known rebreathers (having three oxygen sensors) is as follows:

1. If two oxygen sensors have sensor outputs that are within ±0.2 atm of the rebreather's target set-point and a third oxygen sensor is reading >±0.2 atm away from the target set-point (i.e. because the third sensor is not functioning correctly), then the third oxygen sensor is removed from the voting logic and the averaging takes place based on the outputs of the two other oxygen sensors. Therefore, the $PPO_2$ in the gas in the rebreather is controlled (e.g. oxygen is injected into the gas in the rebreather) based on the average of the two other oxygen sensors, and the output of the third oxygen sensor that is not working correctly is disregarded when determining the average.

2. If all three oxygen sensors are >±0.2 atm from the rebreather's target set-point then all three oxygen sensors are used in the averaging, and the $PPO_2$ in the gas in the rebreather is controlled based on the average of all three oxygen sensors.

SUMMARY OF THE INVENTION

The present inventors have realised that known electronic "voting logic" systems as described above may not correctly determine the $PPO_2$ in some circumstances, for example where more than one of the oxygen sensors is not functioning correctly, e.g. where more than one of the oxygen sensors is current-limited at a current corresponding to a partial pressure of oxygen below the partial pressure of oxygen being measured.

For example, consider an arrangement in which a rebreather has three oxygen sensors, the $PPO_2$ in the gas in the rebreather is at the target set-point of the rebreather, and the outputs of two of the oxygen sensors have become static below the target set-point of the rebreather (but within 0.2 atm of the target set-point). In other words, two of the oxygen sensors are current-limited and are indicating a $PPO_2$ that is lower than the actual $PPO_2$, because they cannot generate sufficient current. The output of the third oxygen sensor is not static (it is not current limited) and is equal to the target set-point (the $PPO_2$ being measured).

Using the simple voting system described above, initially averaging will take place over the outputs of all three of the oxygen sensors, because the outputs of all three of the oxygen sensors are within 0.2 atm of the rebreather's target set-point (as required by the voting logic described above). The average $PPO_2$ determined by the control system will be below the target set-point, because the outputs of the two current-limited oxygen sensors are below the target set-point. Therefore, the control system will control the rebreather to add oxygen to the gas in the rebreather, to increase the determined $PPO_2$ to try to reach the target set-point.

The $PPO_2$ in the gas in the rebreather will increase, as will the output of the third (non-current-limited) oxygen sensor, which is correctly sensing the $PPO_2$ in the gas in the rebreather. However, the outputs of the two current-limited oxygen sensors will remain static as the $PPO_2$ increases, since these oxygen sensors cannot generate any more current. At some point, the output of the third (non-current-limited) oxygen sensor will become >0.2 atm above the target set-point, and this output will therefore be disregarded by the control system when the control system determines the $PPO_2$ in the gas in the rebreather. Instead, the $PPO_2$ in the gas in the rebreather will be determined based on the average of the two current-limited oxygen sensors, which are static below the target set-point (and still within 0.2 atm of the target set-point).

Therefore, the control system will continue to determine that the $PPO_2$ in the gas in the rebreather is below the target set-point and continue to add oxygen to the gas in the rebreather, even though the $PPO_2$ in the gas in the rebreather is above the target set-point and is increasing. As such, the $PPO_2$ in the gas in the rebreather will continue to increase until an unsafe $PPO_2$ is reached, potentially without the user of the breathing apparatus being aware that anything is wrong.

Therefore, the present inventors have realised that with known electronic "voting logic" systems as described above it is possible for the $PPO_2$ in the gas in the rebreather to reach dangerous levels.

The present inventors have realised that this problem may be prevented or overcome by using additional information relating to the operation of the breathing apparatus, in addition to the output of one or more of the oxygen sensors, when controlling the operation of the breathing apparatus.

At its most general, the present invention relates to using additional information relating to the operation of the breathing apparatus, in addition to the output of one or more of the oxygen sensors, when controlling the operation of the breathing apparatus. Therefore, the operation of the breathing apparatus is not controlled solely on the basis of the output of one or more of the oxygen sensors, as in the known systems discussed above. Instead, control of the operation of the breathing apparatus is based on both the output of one or more of the oxygen sensors and on additional information relating to the operation of the breathing apparatus. Therefore, in a case where controlling the operation of the breathing apparatus based solely on the output of one or more oxygen sensors, for example in accordance with a voting logic as discussed above, would lead to abnormal behaviour of the breathing apparatus, this may be prevented by also taking into account the additional information when controlling the operation of the breathing apparatus.

According to a first aspect of the present invention there is provided a controller for controlling a breathing apparatus that comprises a plurality of oxygen sensors, each for sensing an oxygen content of a gas in the breathing apparatus, the controller being configured to control the operation of the breathing apparatus based on the output of one or more of the oxygen sensors and additional information relating to the operation of the breathing apparatus Oxygen content may mean a partial pressure of oxygen in the gas in the breathing apparatus.

Additional information relating to the operation of the breathing apparatus may mean information relating to the operation of the breathing apparatus other than the outputs of the plurality of oxygen sensors. For example, the additional information may be predetermined information or data stored in a memory of the breathing apparatus before operation of the breathing apparatus, or it may be information or data that is derived or calculated during operation of the breathing apparatus, or it may be information or data that is sensed or measured by the breathing apparatus, e.g. by another type of sensor of the breathing apparatus.

According to the first aspect of the present invention, control of the operation of the breathing apparatus is based on both the output of one or more of the oxygen sensors (as in the known systems discussed above) and on the additional information relating to the operation of the breathing apparatus. Using the additional information when controlling the operation of the breathing apparatus may prevent the controller from erroneously controlling the breathing apparatus as might otherwise occur if the control were carried out based only on the outputs of one of more of the oxygen sensors, e.g. as in the example discussed above.

The controller according to the first aspect of the present invention may have any one, or, to the extent that they are compatible, any combination of the following optional features.

The additional information may comprise information stored in a memory of the breathing apparatus in advance of operation of the breathing apparatus. For example, the additional information may be information regarding or characterising one or more components of the breathing apparatus, for example specifying a manufacturing date, and/or an installation date, and/or an initial behaviour or performance of the one or more components. This information may be stored in the memory by a manufacturer of the breathing apparatus or of a component of the breathing apparatus. Alternatively, or in addition, this information may be entered by a user of the breathing apparatus. The memory may be a memory of an oxygen sensor, e.g. a solid state memory of the oxygen sensor.

The additional information may comprise: information relating to an installation date of an oxygen sensor; and/or information relating to an expected operational lifetime of an oxygen sensor; and/or time limits for durations of operation of an oxygen sensor at different oxygen contents; and/or information relating to an initial maximum output of an oxygen sensor. For example, in the example discussed above in which two of the oxygen sensors are current-limited, these oxygen sensors may have been installed a long time ago, and/or may have passed their expected operational lifetime, and/or may have spent a long time sensing a high oxygen content, and/or may have had a relatively low initial maximum output. This information may therefore indicate that there is a risk that these oxygen sensors may not be working correctly and that less weight/importance should be given to the outputs of these oxygen sensors, and/or that their outputs should be excluded when controlling the operation of the breathing apparatus, and/or that some other action should be taken, for example entering a fail-safe mode in which a predetermined amount of oxygen is input to the breathing apparatus, and/or alerting a user of the breathing apparatus, and/or automatically performing a test of the oxygen sensors. One or more of these types of information may be stored/recorded in a memory of the oxygen sensor.

Alternatively, or in addition, the additional information may comprise information (or data) derived (or calculated) during operation of the breathing apparatus. For example, the additional information may comprise: a measurement history of an oxygen sensor; and/or a duration of operation of an oxygen sensor; and/or durations of operation of an oxygen sensor at different oxygen contents. For example, this information may be used to determine whether an oxygen sensor has been operated for longer than its intended operational lifetime, or if it has been used to sense high oxygen contents (which will cause its maximum output to decay more rapidly), or may indicate if an oxygen sensor is current-limited (e.g. because it has output the same current for a long time or for a range of different oxygen contents. One or more of these types of information may be stored/recorded in a memory of the oxygen sensor.

The controller may be for controlling a breathing apparatus that further comprises a different type of sensor for sensing different information relating to the behaviour of the breathing apparatus; and the additional information may comprise an output of the different type of sensor.

A different type of sensor(s) may mean a sensor(s) or a combined sensor(s) and software/hardware system of a type other than an oxygen sensor. A different type of sensor(s) may mean a sensor(s) for sensing something other than oxygen content.

Information relating to the behaviour of the breathing apparatus may mean information relating to an operational (e.g. current) state or performance of the breathing apparatus, for example information that defines or characterises an operational state or performance of the breathing apparatus. Such information may be useful when controlling the operation of the breathing apparatus.

The controller may be configured to control the oxygen content of the gas in the breathing apparatus based on the output of one or more of the oxygen sensors and the additional information relating to the operation of the breathing apparatus. As discussed above, using the additional information in addition to the outputs of one or more of the oxygen sensors when controlling the oxygen content of the gas in the breathing apparatus may improve the control of the oxygen content of the gas. For example, in the situation discussed above where there are three oxygen sensors, two of which are current limited, it may prevent the oxygen content of the gas from being incorrectly controlled based on the outputs of the two current-limited oxygen sensors.

The controller may be configured to identify an oxygen sensor of the plurality of oxygen sensors that is not functioning correctly based on the output of one or more of the oxygen sensors and on the additional information. For example, the additional information may be used as part of a voting logic in determining which oxygen sensor's outputs should be used and which oxygen sensor's outputs should be disregarded when controlling the operation of the breathing apparatus.

The controller may be configured to control the oxygen content of the gas in the breathing apparatus based on the outputs of the plurality of oxygen sensors, excluding the output of any oxygen sensor identified as not functioning correctly. Therefore, the oxygen content of the gas in the breathing apparatus may be more accurately or correctly controlled.

The controller may be configured to: identify an oxygen sensor of the plurality of oxygen sensors as not functioning correctly based on the output of one or more of the oxygen sensors; and control an operation of the breathing apparatus based on the results of this identification and on the additional information. For example, the controller may use a known voting logic as described above to identify an oxygen sensor of the plurality of oxygen sensors as not functioning correctly. In some circumstances, for example in the example discussed above where two of the three oxygen sensors are current-limited, the oxygen sensor identified as not functioning correctly may in fact be functioning correctly. The additional information may be used to verify or check the identification, or to determine if other action should be taken. For example, if the identified oxygen sensor is newly installed and well within its expected lifetime, whereas the oxygen sensors identified as working correctly are relatively old, or outside of their expected lifetimes, it is possible that the identification is incorrect. In this case, the breathing apparatus may take appropriate action. For example, the breathing apparatus may alert a user of the breathing apparatus to this problem, for example by sounding an alarm or issuing an alert. Alternatively, or in addition, the breathing apparatus may enter a fail-safe mode, in which the breathing apparatus is controlled in a predetermined manner, for example in which oxygen is added to the breathing apparatus at a predetermined rate. Alternatively, or in addition, an oxygen sensor test may be instigated, for example a test in which the oxygen content of the gas in the breathing apparatus is varied and the response of the oxygen sensor(s) to this variation is monitored. Suitable oxygen sensor tests are described in more detail below.

The controller may be configured to: control an oxygen content of a gas in the breathing apparatus based on the output of one or more of the plurality of oxygen sensors; detect abnormal behaviour of the breathing apparatus based on the output of the different type of sensor; and control an operation of the breathing apparatus based on the detection of abnormal behaviour of the breathing apparatus.

Abnormal behaviour of the breathing apparatus may mean behaviour of the breathing apparatus that falls outside of expected or predetermined behaviour of the breathing apparatus, for example behaviour that is outside of, or not in accordance with, predetermined parameters. Abnormal behaviour may mean behaviour of the breathing apparatus in which the breathing apparatus does not maintain a substantially constant partial pressure of oxygen in the gas in the breathing apparatus, or behaviour in which the partial pressure of oxygen diverges from a target value of the partial pressure of oxygen in the gas in the breathing apparatus. Abnormal behaviour may mean behaviour of the breathing apparatus in which an abnormal amount of oxygen is added to the gas in the breathing apparatus (i.e. an amount of oxygen above a predetermined upper limit) or in which oxygen is added to the gas in the breathing apparatus at an abnormal rate (i.e. a rate above a predetermined upper limit).

What constitutes normal or abnormal behaviour may depend on the environment in which the breathing apparatus is being used. For example, what constitutes normal or abnormal behaviour may depend on factors such as the rate of metabolism of a user of the apparatus (which may affect the amount of oxygen used by the use), a depth or depth change of the user (and therefore the absolute pressure of the environment surrounding the breathing apparatus), or other variables. Suitable parameters for defining what constitutes normal or abnormal behaviour may be measured or determined in advance based on the environment in which the apparatus is being used, and/or based on other factors.

Therefore, in some embodiments the controller is configured to control an oxygen content of a gas in the breathing apparatus based on the output of one or more of the plurality of oxygen sensors. In this respect, the controller may be configured to use an electronic "voting logic" system the same as, or similar to, that described above in relation to known control systems to determine which of the outputs of the plurality of oxygen sensors should be taken into account when controlling the oxygen content of the gas in the breathing apparatus and which (if any) should be disregarded. Of course, the controller according to the first aspect of the present invention may instead use a different "voting logic" system.

In addition, in some embodiments the controller is configured to detect abnormal behaviour of the breathing apparatus based on the output of the different type of sensor, and to control an operation of the breathing apparatus based on the detection of abnormal behaviour of the breathing apparatus. Therefore, where control of the oxygen content of the gas in the breathing apparatus based on the output of one or more of the plurality of oxygen sensors leads to abnormal operation of the breathing apparatus (as in the example above where the partial pressure of oxygen in the gas in the breathing apparatus is continually increased, because of the static outputs of the two current-limited oxygen sensors), the abnormal operation of the breathing apparatus can be detected, and appropriate action can be taken, for example to alert a user and/or to take action to try to correct the abnormal behaviour or to perform one or more diagnostic tests. Trying to correct the abnormal behaviour may comprise changing an operation of the breathing apparatus, to try to inhibit the abnormal behaviour of the breathing apparatus.

Essentially, detecting whether or not the behaviour of the breathing apparatus is abnormal can be used as a check on whether or not the controller is correctly controlling the oxygen content of the gas in the breathing apparatus. If it is determined that the behaviour of the breathing apparatus is abnormal, and therefore that the controller is not correctly controlling the oxygen content of the gas in the breathing apparatus (as in the example discussed above, in which the oxygen content keeps increasing), appropriate action can be taken, e.g. to notify the user or to try to correct the control of the oxygen content, for example by changing one or more parameters of the operation of the breathing apparatus to correct for the abnormal behaviour, or by carrying out a diagnostic test.

For example, in the example discussed above, when the two sensors become static/current limited below the actual partial pressure of oxygen in the gas in the breathing apparatus, the simplistic logic voting rules in which the outputs of all three oxygen sensors are averaged lead to the control system underestimating the partial pressure of oxygen, and therefore causing more oxygen to be injected into the gas in the breathing apparatus. This may lead to an increase in the fire rate of a solenoid controlling the input of gas to the breathing apparatus. When the third oxygen sensor, which is working correctly, is voted out of the averaging due to the logic voting rules (i.e. because its output is >0.2 atm from the target set-point) the fire rate of the solenoid may continue to increase as the amount of oxygen injected into the breathing apparatus continues to increase (since the target set-point is never reached). By detecting the resulting abnormally high fire rate of the solenoid (e.g. relative to a predetermined normal solenoid fire rate during normal operation of the breathing apparatus, established based on e.g. metabolism and depth changes), it may be determined that the behaviour of the breathing apparatus is abnormal, e.g. that the controller is not correctly controlling the partial pressure of oxygen in the breathing apparatus. Once it has been detected that the behaviour of the breathing apparatus is abnormal, appropriate action may be taken, e.g. to notify the user or to correct or improve the operation or behaviour of the breathing apparatus. Of course, in other examples of the present invention the different type of sensor may sense different information relating to the behaviour of the breathing apparatus, instead of the fire rate of the solenoid controlling the input of gas to the breathing apparatus.

The controller may be configured to detect that the behaviour of the breathing apparatus is abnormal where: the output of the different type of sensor is above a predetermined upper limit; or the output of the different type of sensor is below a predetermined lower limit.

Where the controller detects that the behaviour of the breathing apparatus is abnormal, the controller may be configured to: change an operation of the breathing apparatus to inhibit the abnormal behaviour of the breathing apparatus; or change an operation of the breathing apparatus to enter a failsafe mode, in which the operation of the breathing apparatus is controlled in a predetermined way.

Therefore, the controller may take corrective action to change the operation of the breathing apparatus so that the behaviour of the breathing apparatus is no longer abnormal, for example by altering an amount of oxygen being added to the gas in the breathing apparatus, or a rate at which oxygen is being added to the gas in the breathing apparatus, or another parameter. This corrective action may override the control of the breathing apparatus that would otherwise occur based on a simple voting logic as discussed above. The corrective action may comprise entering a failsafe mode in which the operation of the breathing apparatus is controlled in a predetermined way, for example in which the breathing apparatus is controlled to provide the minimum environment (e.g. injection of oxygen into the gas in the rebreather) necessary for life support.

Where the controller detects that the behaviour of the breathing apparatus is abnormal, the controller may be configured to alert a user of the breathing apparatus. This may be in addition to, or as an alternative to, the corrective action discussed above. For example, the controller may be configured to alert the user using a command based alarm (that commands the user to take a corrective action), or a different type of alarm. The alarm may alert the user to the fact that the behaviour of the breathing apparatus is abnormal, and that the controller may not be correctly controlling the oxygen content of the gas in the breathing apparatus, and that the user should therefore take remedial action.

Where the controller detects that the behaviour of the breathing apparatus is abnormal, the controller may be configured to instigate an oxygen sensor test for determining if any of the plurality of oxygen sensors is not functioning correctly. This may be in addition to, or as an alternative to, the other actions discussed above. As discussed above, abnormal operation of the breathing apparatus may suggest that the controller is incorrectly controlling the oxygen content of the breathing apparatus, e.g. because the voting logic is incorrectly identifying which of the oxygen sensors is not functioning correctly (as in the example discussed above, where the third oxygen sensor that is working correctly is incorrectly identified as not working correctly). Therefore, when the controller detects that the behaviour of the breathing apparatus is abnormal, the controller may instigate an oxygen sensor test to determine which, if any, of the oxygen sensors is not functioning correctly (e.g. is current limited at a current corresponding to a partial pressure below the partial pressure being measured). An oxygen sensor test may mean a test for testing one or more of the oxygen sensors, e.g. a test for testing that the one or more oxygen sensor outputs a substantially correct output. The results of the oxygen sensor test may indicate which oxygen sensors are not working correctly, and the oxygen content of the gas in the breathing apparatus may then be controlled based only on the oxygen sensor(s) of the plurality of oxygen sensors that are identified as working correctly (i.e. oxygen sensors that are identified as not working correctly based on the results of the oxygen sensor test may be removed from the voting logic equation). In this manner, the controller may control the oxygen content of the gas in the breathing apparatus based on the outputs of only those oxygen sensors that are identified as working correctly, and the behaviour of the breathing apparatus may consequently return to normal.

The controller may be configured to: control the breathing apparatus to lower the oxygen content of the gas in the breathing apparatus; and identify an oxygen sensor of the plurality of oxygen sensors as not functioning correctly where the output of the oxygen sensor is substantially the same for a range of different oxygen contents of the gas in the breathing apparatus. This is an example of an oxygen sensor test.

For example, where an oxygen sensor is current-limited, the output of the oxygen sensor may remain substantially the same (i.e. at the maximum output of the oxygen sensor) as the oxygen content of the gas is reduced, until the oxygen content falls below an oxygen content corresponding to the current at which the oxygen sensor is limited (i.e. the maximum current that the oxygen sensor can provide), at which point the oxygen sensor may begin to function correctly again (i.e. to provide an output that corresponds to the oxygen content). Therefore, an oxygen sensor that is not working correctly, e.g. an oxygen sensor that is current limited at a current corresponding to a partial pressure below the partial pressure being measured, may be identified if its output remains substantially the same over a range of oxygen contents.

The controller may be further configured to: subsequently control the breathing apparatus to raise the oxygen content of the gas in the breathing apparatus; and confirm that the identified oxygen sensor is not functioning correctly where the output of the oxygen sensor is substantially the same for a range of different oxygen contents of the gas in the breathing apparatus.

This may provide an additional check that an identified oxygen sensor is not working correctly. For example, as the oxygen content of the gas is increased, the output of the identified oxygen sensor may increase until it reaches the maximum output of the oxygen sensor (i.e. the output at which the oxygen sensor is current-limited). The output of the oxygen sensor may then stay substantially the same as the oxygen content of the gas is further increased, because the oxygen sensor is current-limited.

Where the controller does not detect that the behaviour of the breathing apparatus is abnormal, the controller may be configured to identify an oxygen sensor of the plurality of oxygen sensors that is not functioning correctly based on the outputs of the plurality of oxygen sensors and on a predetermined target oxygen content of the gas in the breathing apparatus. For example, the breathing apparatus may be configured to identify an oxygen sensor that is not functioning correctly based on the differences between the outputs of the plurality of oxygen sensors and the predetermined target oxygen content. This may involve an assessment of whether or not the outputs of each of the oxygen sensors is within a predetermined range of the predetermined target oxygen content.

The controller may be configured to: determine if a majority of the outputs of the plurality of oxygen sensors are within a predetermined range of a predetermined output; and if so, determine that any of the plurality of oxygen sensors having an output not within the predetermined range of the predetermined output is not functioning correctly.

For example, the controller may implement the basic voting logic discussed above in relation to known breathing apparatus, in which an oxygen sensor is voted out of the voting logic if its output is outside of a predetermined range from a predetermined output and the outputs of the other oxygen sensors are within the predetermined range from the predetermined output. Of course, a different type of voting logic may be used instead in the present invention.

The controller may be configured to control the oxygen content of the gas in the breathing apparatus based on the outputs of the plurality of oxygen sensors, excluding the output of any oxygen sensor identified as not functioning correctly.

The controller may be configured to determine the oxygen content of the gas in the breathing apparatus based on the outputs of the plurality of oxygen sensors, excluding the output of any oxygen sensor identified as not functioning correctly. For example, the controller may average the outputs of the plurality of oxygen sensors, excluding the output of any oxygen sensor identified as not functioning correctly.

The controller may be configured to control the oxygen content of the gas in the breathing apparatus based on a comparison of the determined oxygen content of the gas in the breathing apparatus and a predetermined target oxygen content. For example, the controller may be configured to control the oxygen content of the gas in the breathing apparatus to be substantially the same as the predetermined target oxygen content, and may increase the rate at which oxygen is added to the gas in the breathing apparatus where the oxygen content of the gas in the breathing apparatus is below the predetermined target oxygen content.

The controller may be for controlling a breathing apparatus comprising a plurality of different types of sensor for sensing different information relating to the behaviour of the breathing apparatus; and the controller may be configured to detect abnormal behaviour of the breathing apparatus based on the outputs of more than one of the plurality of different types of sensor.

Therefore, the outputs of more than one type of other sensor may be used to detect abnormal behaviour of the breathing apparatus. Using a second different type of sensor to detect abnormal behaviour of the breathing apparatus may provide additional verification that the behaviour of the breathing apparatus is abnormal. In addition, or alternatively, the output of the second different type of sensor may be used to account for environmental changes that may affect what constitutes a normal operation of the breathing apparatus. For example, the second different type of sensor may be used to determine the depth of the breathing apparatus in a liquid or gas, or the absolute pressure of a liquid or gas in which the breathing apparatus is submerged, which may affect the output of an oxygen sensor.

There may be provided a breathing apparatus comprising: a plurality of oxygen sensors, each for sensing an oxygen content of a gas in the breathing apparatus; and a controller according to any one of the previous claims arranged to control the breathing apparatus.

The breathing apparatus may further comprise a different type of sensor for sensing different information relating to the behaviour of the breathing apparatus.

The different type of sensor may be for: sensing a depth of the breathing apparatus in a liquid or gas when the breathing apparatus is submerged in the liquid or gas; and/or sensing a rate of change of a depth of the breathing apparatus in a liquid or gas when the breathing apparatus is submerged in the liquid or gas; and/or sensing an absolute pressure of a liquid or gas when the breathing apparatus is submerged in the liquid or gas; and/or sensing a content of gas in a container of pressurised gas for inputting pressurised gas into the breathing apparatus; and/or sensing a pressurised gas usage rate of the breathing apparatus; and/or sensing a volume of pressurised gas input into the breathing apparatus; and/or sensing an injection fire rate of a device controlling input of a pressurised gas into the breathing apparatus; and/or sensing a pressure of the gas in the breathing apparatus; and/or sensing a breathing rate of a user of the breathing apparatus; and/or sensing a rate of usage of oxygen of a user of the breathing apparatus; and/or sensing a volume of gas breathed by a user of the breathing apparatus. Of course, the different type of sensor may be for sensing some other parameter of the breathing apparatus.

A device controlling input of the pressurised gas into the breathing apparatus may comprise a solenoid, or may comprise another type of device, for example another type of mechanical and/or electrical means, such as a mechanical and/or electrical device, controller or valve. Controlling input of the pressurised gas into the breathing apparatus may comprise controlling a volume of gas input into the breathing apparatus. For an electrical means, such as a solenoid valve, it may be advantageous to sense both an injection fire rate of the electrical means (e.g. the solenoid) and a volume of gas input into the breathing apparatus by the electrical means (although it may be sufficient to sense only one of these). For a mechanical means, it may be advantageous to sense a volume of gas input into the breathing apparatus by the mechanical means.

For example, the volume of pressurised gas input into the breathing apparatus (or the injection fire rate of a device such as a solenoid or a mechanical valve controlling input of a pressurised gas into the breathing apparatus) may increase content is below the target set-point and therefore keeps inputting additional oxygen into the gas in the breathing apparatus. The pressurised gas usage rate may also increase in these circumstances. Therefore, these parameters may be used to identify abnormal operation of the breathing apparatus in which the oxygen content of the gas in the breathing apparatus continually increases. Of course, other types of information may also be used instead of, or in addition to, this information.

The breathing apparatus may comprise a plurality of different types of sensor for sensing different information relating to the behaviour of the breathing apparatus. For example, the breathing apparatus may measure or detect both the volume of pressurised gas input into the breathing apparatus and the pressurised gas usage rate, and both of these measurements may be used to detect abnormal operation of the breathing apparatus.

The breathing apparatus may be a rebreather, i.e. a breathing apparatus in which the used gas is recycled or reused.

According to a second aspect of the present invention there is provided a method of controlling a breathing apparatus that comprises a plurality of oxygen sensors, each for sensing an oxygen content of a gas in the breathing apparatus, the method comprising controlling the operation of the breathing apparatus based on the output of one or more of the oxygen sensors and additional information relating to the operation of the breathing apparatus.

The additional information may comprise information stored in a memory of the breathing apparatus in advance of operation of the breathing apparatus.

The additional information may comprise: information relating to an installation date of an oxygen sensor; and/or information relating to an expected operational lifetime of an oxygen sensor; and/or time limits for durations of operation of an oxygen sensor at different oxygen contents; and/or information relating to an initial maximum output of an oxygen sensor.

The additional information may comprise information derived during operation of the breathing apparatus.

The additional information may comprise: a measurement history of an oxygen sensor; and/or a duration of operation of an oxygen sensor; and/or durations of operation of an oxygen sensor at different oxygen contents.

The method may be a method of controlling a breathing apparatus that further comprises a different type of sensor for sensing different information relating to the behaviour of the breathing apparatus; and the additional information may comprise an output of the different type of sensor.

The method may comprise controlling the oxygen content of the gas in the breathing apparatus based on the output of one or more of the oxygen sensors and the additional information relating to the operation of the breathing apparatus.

The method may comprise identifying an oxygen sensor of the plurality of oxygen sensors that is not functioning correctly based on the output of one or more of the oxygen sensors and on the additional information.

The method may comprise controlling the oxygen content of the gas in the breathing apparatus based on the outputs of the plurality of oxygen sensors, excluding the output of any oxygen sensor identified as not functioning correctly.

The method may comprise: identifying an oxygen sensor of the plurality of oxygen sensors as not functioning correctly based on the output of one or more of the oxygen sensors; and controlling an operation of the breathing apparatus based on the results of this identification and on the additional information.

The method may comprise: controlling an oxygen content of a gas in the breathing apparatus based on the output of one or more of the plurality of oxygen sensors; detecting abnormal behaviour of the breathing apparatus based on the output of the different type of sensor; and controlling an operation of the breathing apparatus based on the detection of abnormal behaviour of the breathing apparatus.

The method may comprise detecting that the behaviour of the breathing apparatus is abnormal where: the output of the different type of sensor is above a predetermined upper limit; or the output of the different type of sensor is below a predetermined lower limit.

Where it is detected that the behaviour of the breathing apparatus is abnormal, the method may comprise: changing an operation of the breathing apparatus to inhibit the abnormal behaviour of the breathing apparatus; or changing an operation of the breathing apparatus to enter a failsafe mode, in which the operation of the breathing apparatus is controlled in a predetermined way.

Therefore, the method may comprise taking corrective action to inhibit (or correct) the abnormal behaviour of the breathing apparatus, by changing the operation of the breathing apparatus so that the behaviour of the breathing apparatus returns to normal. This may override the control of the breathing apparatus that would otherwise occur based on a simple voting logic system as discussed above.

Where it is detected that the behaviour of the breathing apparatus is abnormal, the method may comprise alerting a user of the breathing apparatus. For example, the method may comprise alerting the user using a command based alarm.

The method may comprise instigating (or carrying out) an oxygen sensor test for determining if any of the plurality of oxygen sensors is not functioning correctly where it is detected that the behaviour of the breathing apparatus is abnormal.

Where it is detected that the behaviour of the breathing apparatus is abnormal, the method may comprise: controlling the breathing apparatus to change the oxygen content of the gas in the breathing apparatus; and identifying an oxygen sensor of the plurality of oxygen sensors that is not functioning correctly based on the response of the oxygen sensor to the change in the oxygen content of the gas in the breathing apparatus.

The method may comprise: controlling the breathing apparatus to lower the oxygen content of the gas in the breathing apparatus; and identifying an oxygen sensor of the plurality of oxygen sensors as not functioning correctly where the output of the oxygen sensor is substantially the same for a range of different oxygen contents of the gas in the breathing apparatus.

The method may comprise: subsequently controlling the breathing apparatus to raise the oxygen content of the gas in the breathing apparatus; and confirming that the identified oxygen sensor is not functioning correctly where the output of the oxygen sensor is substantially the same for a range of different oxygen contents of the gas in the breathing apparatus.

Where it is not detected that the behaviour of the breathing apparatus is abnormal, the method may comprise identifying an oxygen sensor of the plurality of oxygen sensors that is not functioning correctly based on the outputs of the plurality of oxygen sensors and on a predetermined target oxygen content of the gas in the breathing apparatus.

The method may comprise: determining if a majority of the outputs of the plurality of oxygen sensors are within a predetermined range of a predetermined output; and if so, determining that any of the plurality of oxygen sensors having an output not within the predetermined range of the predetermined output is not functioning correctly.

The method may comprise controlling the oxygen content of the gas in the breathing apparatus based on the outputs of the plurality of oxygen sensors, excluding the output of any oxygen sensor identified as not functioning correctly.

The method may comprise determining the oxygen content of the gas in the breathing apparatus based on the outputs of the plurality of oxygen sensors, excluding the output of any oxygen sensor identified as not functioning correctly.

The method may comprise controlling the oxygen content of the gas in the breathing apparatus based on a comparison of the determined oxygen content of the gas in the breathing apparatus and a predetermined target oxygen content.

The method may be a method of controlling a breathing apparatus that comprises a plurality of different types of sensor for sensing other information relating to the behaviour of the breathing apparatus; and the method may comprise detecting abnormal behaviour of the breathing apparatus based on the outputs of more than one of the plurality of different types of sensor.

The different type of sensor may sense: a depth of the breathing apparatus in a liquid or gas when the breathing apparatus is submerged in the liquid or gas; and/or a rate of change of a depth of the breathing apparatus in a liquid or gas when the breathing apparatus is submerged in the liquid or gas; and/or an absolute pressure of a liquid or gas when the breathing apparatus is submerged in the liquid or gas; and/or a content of gas in a container of pressurised gas for inputting pressurised gas into the breathing apparatus; and/or a pressurised gas usage rate of the breathing apparatus; and/or a volume of pressurised gas input into the breathing apparatus; and/or an injection fire rate of a device controlling input of a pressurised gas into the breathing apparatus; and/or a pressure of the gas in the breathing apparatus; and/or a breathing rate of a user of the breathing apparatus; and/or a rate of usage of oxygen of a user of the breathing apparatus; and/or a volume of gas breathed by a user of the breathing apparatus.

The method may be a method of controlling a rebreather.

There may be provided a computer program comprising computer program code adapted to perform the method according to the second aspect of the invention when executed on a data processing system.

In any of the embodiments described above, the oxygen sensor may have a memory, for example a solid state memory, for storing data or information. Therefore, the oxygen sensor may be a so-called "intelligent" oxygen sensor. For example, as discussed above, the additional information relating to the operation of the breathing apparatus may be information relating to the oxygen sensor stored in a memory of the oxygen sensor.

In some embodiments, the oxygen sensor may have identification information stored in a memory thereof. The identification information may identify a manufacturer of the oxygen sensor. In addition, or alternatively, the identification information may identify a particular model, type or class of the oxygen sensor. In addition, or alternatively, the identification information may identify a particular model, type or class of breathing apparatus in which the oxygen sensor can be used, i.e. with which the oxygen sensor is compatible. In addition, or alternatively, the identification information may uniquely identify the oxygen sensor.

The identification number may comprise a serial number, which may comprise a string of characters, for example letters and/or numbers. For example, in one embodiment the identification number may comprise a first string of characters identifying a manufacturer of the oxygen sensor and a second string of characters uniquely identifying the oxygen sensors. The first and second strings of characters may be combined to form a single identification code.

The breathing apparatus may be configured so that the controller obtains the identification information of an oxygen sensor from the oxygen sensor. For example, the controller of the breathing apparatus may be configured to request the identification information from the oxygen sensor. Alternatively, the oxygen sensor may be configured to provide this information to the controller without requiring such a request. This may be configured to occur at, or at a predetermined time after, the time at which an oxygen sensor is newly connected to the controller.

In some embodiments, the controller may be configured to use the identification information obtained from the oxygen sensor to determine if the oxygen sensor can be used with the breathing apparatus, i.e. whether or not the oxygen sensor is compatible with the breathing apparatus. This may be achieved by the controller comparing the identification information obtained from the oxygen sensor with other information stored in a memory of the controller or breathing apparatus. For example, a memory of the controller may have stored therein a list of identification information of oxygen sensors that are compatible with the breathing apparatus, or information identifying the model, type or class of the breathing apparatus. Alternatively, the controller may comprise a program or algorithm for determining from the identification information whether or not the oxygen sensor is compatible with the breathing apparatus.

As discussed above, other types of information may also be stored in the memory of the oxygen sensor. For example, the memory of the oxygen sensor may store information about a calibration of the oxygen sensor, such as a date on which the sensor was calibrated, and/or information about the results of the calibration. For example, when an oxygen sensor is connected to the controller for the first time, the controller may automatically (for example based on the recognition of new identification information of a newly added oxygen sensor) perform a calibration of the oxygen sensor. Alternatively, or in addition, a user may manually request a calibration of the sensor, or the controller may perform calibration periodically or intermittently.

The date of the calibration may be stored in the memory of the oxygen sensor. A plurality of calibration dates may be stored in the memory of the oxygen sensor in the form of a calibration log. In addition, or alternatively, a result(s) of the calibration may be stored in the memory, for example in association with the calibration date. For example, the memory may store a reading of the oxygen sensor in a particular environment (e.g. ambient air) following the calibration. In addition, or alternatively, a calibration constant(s) (such as an offset and/or a gain) determined during the calibration may be stored in the memory. Such information about the calibration of the oxygen sensor may be an example of the additional information relating to the operation that is used by the controller to control the operation of the breathing apparatus.

An advantage of storing such calibration information in the memory of the oxygen sensor, and indeed more generally of storing information relating to the oxygen sensor in the memory of the oxygen sensor, is that this information will still be directly associated with the oxygen sensor if the oxygen sensor is moved to a different connection position in the breathing apparatus (e.g. switched in position with another of the plurality of oxygen sensors, or simply moved to replace another of the plurality of oxygen sensors) or indeed moved to a different breathing apparatus altogether. Thus, for example, the (new) breathing apparatus will automatically be able to use the oxygen sensor without having to perform a further calibration and/or other processes that may be required for a newly connected oxygen sensor that doesn't have such information stored in the memory thereof.

Other information, such as the number of hours for which the oxygen sensor has been used, or the number of hours in which it has been used in a specific environment(s), or its date of manufacture or installation, may also be recorded in the memory of the oxygen sensor. Thus, if the oxygen sensor is moved to another breathing apparatus, or to a new position in the existing breathing apparatus, this information will be available to the controller. Such information may be used to identify or indicate an oxygen sensor that is nearing the end of its operational life (e.g. because it is too old or has been used for too many hours).

Where the controller identifies an oxygen sensor that is not functioning correctly, information indicating this may be recorded in a memory of the oxygen sensor. For example, the controller may be configured to record information indicating that the oxygen sensor should no longer be used in a breathing apparatus in the memory of the oxygen sensor. In other words, an oxygen sensor that is not functioning correctly may be updated with a "failure code" or "do not use warning", which indicates that the oxygen sensor is reaching the end of its operational life or is exhibiting a failure mode. This information may function as an imbedded alarm or warning in the oxygen sensor to prevent subsequent use of the oxygen sensor. An advantage of recording this information in the memory of the oxygen sensor is that this information will be available to the controller of another breathing apparatus if the oxygen sensor is subsequently moved to another breathing apparatus.

The controller may be configured to check (read) the memory of an oxygen sensor to see if any information indicating that the oxygen sensor should no longer be used is recorded in the memory of the oxygen sensor. If the controller detects such information, it may take appropriate action in response. For example, the controller may alert the user of the breathing apparatus, for example with an audible and/or visual alert or warning. In addition, or alternatively, the controller may disregard data from the oxygen sensor when controlling the operation of the breathing apparatus. This may be configured to occur when an oxygen sensor is newly connected to the controller.

Alternatively, the oxygen sensor may be configured to automatically send any information stored in the memory of the oxygen sensor indicating that the oxygen sensor should no longer be used that is to the controller, for example when the oxygen sensor is newly connected to the controller.

BRIEF DESCRIPTION OF THE DRAWINGS

Embodiments of the present invention will now be discussed, by way of example only, with reference to the accompanying FIGURE, in which.

DETAILED DESCRIPTION

Figure 1:
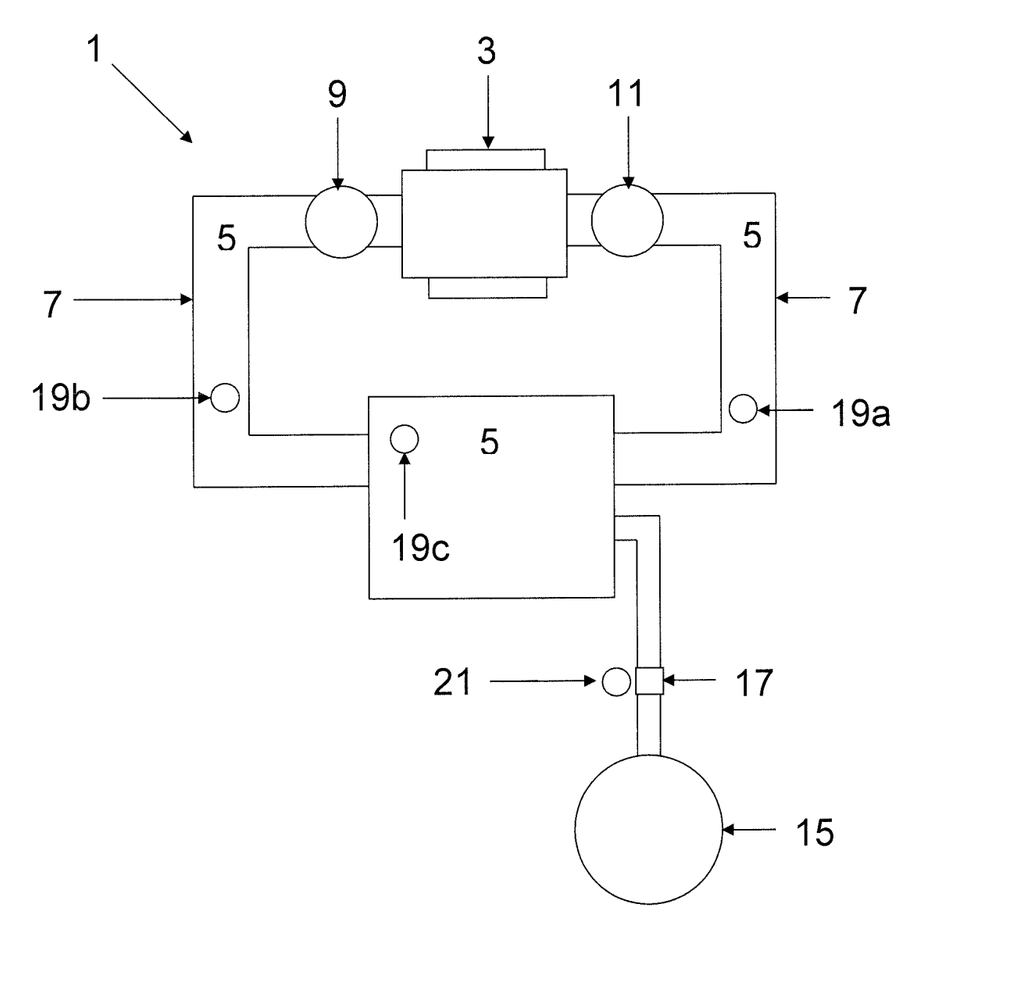
FIG. 1 is a schematic illustration of a portion of a rebreather having a controller according to an embodiment of the present invention.

FIG. 1 is a schematic illustration of a rebreather 1 having a controller according to an embodiment of the present invention. Of course, the rebreater 1 may have many more parts or components than those illustrated in FIG. 1, and the arrangement, shape, etc. of the rebreather 1 and its parts or components may be different to that illustrated in FIG. 1.

FIG. 1 shows a rebreather 1 having a mouthpiece 3 through which a user of the rebreather 1 can breathe a gas 5 in the rebreather. The gas 5 is supplied to the mouthpiece 3 via a breathing loop 7 and an upstream check valve 9. When the user exhales through the mouthpiece, the exhaled gas 5 is removed from the mouthpiece 3 via a downstream check valve 11 and the breathing loop 7. When the user breathes the gas 5, oxygen in the gas 5 is used by the user and therefore removed from the gas 5. Therefore, oxygen is added to the gas 5 from a pressurised container 15 of oxygen via a solenoid valve 17, in order to replenish the oxygen used by the user. The solenoid valve 17 can be controlled to allow a predetermined amount (volume) or rate of oxygen into the gas 5 in the rebreather 1. Of course, in other embodiments, a different means or device may be used to control the addition of oxygen to the gas 5 in the rebreather 1. For example, in other embodiments a mechanical valve or controller, or a different type of electrical or mechanical valve or controller, may be used instead of a solenoid valve 17.

In this embodiment, the rebreather 1 has three oxygen sensors 19a, 19b, 19c, each of which is arranged to sense a partial pressure of oxygen in the gas 5 in the rebreather 1. Of course, in other embodiments there may be a different number of oxygen sensors 19a, 19b, 19c, and the oxygen sensors 19a, 19b, 19c may be differently positioned.

The rebreather 1 may also have a different type of sensor for sensing a volume of oxygen added to the gas 5 in the rebreather. For example, the rebreather may have a sensor 21 for sensing the fire rate of the solenoid valve 17 that controls the addition of pressurised oxygen from the pressurised container 15 to the gas 5 in the rebreather 1. In other embodiments the different type of sensor may sense something other than the volume of oxygen added to the gas 5 in the rebreather 1 (and therefore may be located in a different place in the rebreather 1), and/or there may be more than one type of different sensor.

A normal solenoid valve fire rate, for example a solenoid valve fire rate that would lead to the oxygen content of the gas 5 in the rebreather 1 remaining substantially constant, may be determined in advance. For example, a normal solenoid valve fire rate may be determined by measuring the solenoid valve fire rate when all three of the oxygen sensors 19a, 19b, 19c are functioning correctly and the oxygen content of the gas 5 in the rebreather 1 is remaining substantially constant. Alternatively, a normal solenoid valve fire rate may be calculated, for example based on parameters such as an expected or measured rate of metabolism of the user of the rebreather 1, the depth or rate of depth change of the rebreather 1 (and therefore the absolute pressure and rate of absolute pressure change), and/or based on other factors that may affect the normal solenoid valve fire rate.

The rebreather 1 has a controller (not shown) for controlling the operation of the rebreather 1, for example for controlling the oxygen content of the gas 5 in the rebreather 1.

Initially, the controller may control the partial pressure of oxygen in the gas 5 in the rebreather 1 based on the output of one or more of the plurality of oxygen sensors 19a, 19b, 19c. In this embodiment, the controller may identify any of the plurality of oxygen sensors 19a, 19b, 19c that is not working correctly, for example that is outputting a static output because it is current-limited at a partial pressure less than the partial pressure being measured, based on the outputs of the plurality of oxygen sensors 19a, 19b, 19c and on a predetermined target partial pressure. For example, the controller may use a voting logic as discussed above in relation to known rebreathers to identify any oxygen sensors 19a, 19b, 19c that are not working correctly. For example, where the outputs of two of the oxygen sensors 19a, 19b, 19c are within a predetermined range of a predetermined output, and the output of the third oxygen sensor 19a, 19b, 19c is outside of the predetermined range of the predetermined output, the third oxygen sensor 19a, 19b, 19c may be identified as not working correctly. Therefore, the output of the third oxygen sensor 19a, 19b, 19c may be disregarded and the partial pressure of oxygen in the gas 5 in the rebreather 1 may be determined by averaging the outputs of the other two oxygen sensors 19a, 19b, 19c.

Where the controller determines that the partial pressure of oxygen in the gas 5 in the rebreather 1 is less than a predetermined target partial pressure of oxygen (a target set-point), the controller may control the rebreather 1 to add more oxygen to the gas 5 in the rebreather 1, to try to increase the oxygen content of the gas 5 in the rebreather 1 to be equal to the target set-point. Alternatively, where the controller determines that the partial pressure of oxygen in the gas 5 in the rebreather 1 is above the target set-point, the controller may reduce the amount of oxygen being added to the gas 5 in the rebreather 1, to try to reduce the oxygen content of the gas 5 to be the same as the target set-point.

Where the controller correctly identifies which of the oxygen sensors 19a, 19b, 19c is working correctly, and therefore appropriately controls the amount of oxygen that is added to the gas 5 in the rebreather 1 (and/or the rate at which oxygen is added to the gas 5 in the rebreather 1), the rebreather 1 may behave normally, in the sense that the oxygen content of the gas 5 in the rebreather 1 may remain substantially constant and not diverge from a target set-point of the rebreather 1. In this case, the solenoid valve fire rate may remain substantially constant at the normal level, and the controller may not detect abnormal operation of the rebreather 1.

However, in a situation where two of the oxygen sensors 19a, 19b, 19c become current limited at a partial pressure below the partial pressure being measured, so that their outputs become static, the controller may not correctly control the oxygen content of the gas 5 in the rebreather 1. For example, consider a situation where two of the oxygen sensors 19a, 19b, 19c are current limited at an output below the target set-point (but within the predetermined limits from the target set-point set by the voting system) and the third oxygen sensor 19a, 19b, 19c is not current limited, i.e. it is correctly measuring the partial pressure of oxygen. When the partial pressure of oxygen in the gas 5 in the rebreather 1 is at the target set-point, the third oxygen sensor 19a, 19b, 19c will output the target set-point, and the two current-limited oxygen sensors 19a, 19b, 19c will output a partial pressure below the target set-point. According to the voting logic, the outputs of all three oxygen sensors 19a, 19b, 19c may be averaged, and the controller may therefore incorrectly determine that the partial pressure is below the target set-point. Therefore, the controller will control the rebreather 1 to add more oxygen to the gas 5 in the rebreather 1, to try to increase the partial pressure to be equal to the target set-point. The solenoid valve fire rate will increase as more oxygen is added to the gas 5, but not significantly so. Therefore, the controller may not determine that the operation of the rebreather 1 is abnormal.

As the partial pressure of oxygen in the gas 5 in the rebreather 1 increases, the output of the third oxygen sensor 19a, 19b, 19c will increase, while the outputs of the other two oxygen sensors 19a, 19b, 19c may remain static below the target set-point (because they are current-limited). Therefore, at some point according to the voting logic rules the output of the third oxygen sensor 19a, 19b, 19c will be disregarded, because the third oxygen sensor 19a, 19b, 19c will be identified as not working correctly (even though in fact it is the only oxygen sensor 19a, 19b, 19c that is working correctly). Therefore, the controller will then determine the partial pressure of oxygen based on the outputs of the two current-limited oxygen sensors 19a, 19b, 19c, and as such will continue to add oxygen to the gas 5 in the rebreather 1. Therefore, the solenoid valve fire rate will continue to increase, since the target set-point can never be reached. Changes in absolute pressure (which may affect $PPO_2$, even with static sensors) may be accounted for in this scenario by also sensing or measuring the depth of the rebreather 1. The high solenoid valve fire rate indicates that an abnormal amount of oxygen is being added to the gas 5 in the rebreather (i.e. an amount higher than is necessary to maintain the partial pressure at the target set-point).

Therefore, by sensing the solenoid valve fire rate, and e.g. by comparing it to a predetermined normal solenoid valve fire rate, the controller can detect that the behaviour of the rebreather 1 is abnormal, and that something is going wrong with the control of the partial pressure of oxygen in the gas 5 in the rebreather 1. In addition to the solenoid valve fire rate (i.e. as an additional verification), or as an alternative, the usage rate of pressurised oxygen by the rebreather 1 may also be measured or determined, and used to detect abnormal operation of the rebreather 1.

Once abnormal behaviour of the rebreather 1 has been detected, the controller may control an operation of the rebreather 1 based on this detection. For example, the controller may control the rebreather 1 to try to correct the abnormal behaviour of the rebreather 1, to try to inhibit the abnormal behaviour, and/or perform a diagnostic test, and/or to warn a user of the rebreather 1 that remedial action is required.

For example, in one embodiment, where the controller determines that the solenoid valve fire rate of the rebreather 1 is abnormally high, and that an abnormal (unnecessarily high) amount of oxygen is therefore being added to the gas 5 in the rebreather 1, the controller may reduce the solenoid valve fire rate, to inhibit the abnormally high solenoid valve fire rate and to therefore reduce the amount of oxygen being added to the gas 5 in the rebreather 1. Therefore, the controller may take corrective action to override the control of the rebreather 1 that would otherwise occur based on the simple voting logic discussed above (which would lead to the solenoid valve fire rate continually increasing). Alternatively, the controller may cause the rebreather 1 to enter a fail-safe mode in which the solenoid valve fire rate is set to a predetermined value suitable for providing minimal life support injection volumes.

In addition, or alternatively, the controller may warn a user of the rebreather 1 that the behaviour of the rebreather 1 is abnormal and that remedial action may be required. For example, the rebreather 1 may issue an alarm to the user, for example an alarm issued in a command based format such as "Do Dilutent Flush Now" to instruct the user to take remedial action, such as manually performing a test of the oxygen sensors.

In addition, or alternatively, an oxygen sensor test can be automatically performed upon detection of abnormal behaviour of the rebreather 1, to identify which of the oxygen sensors 19a, 19b, 19c is working correctly, and which, if any, is current-limited. The test may involve lowering the target set-point so that the partial pressure of oxygen in the gas 5 in the rebreather 1 is reduced. Where the output of an oxygen sensor 19a, 19b, 19c remains substantially static as the partial pressure of oxygen is reduced, until a sufficiently low partial pressure is reached that the oxygen sensor 19a, 19b, 19c starts to work again, the oxygen sensor 19a, 19b, 19c may be identified as not working correctly (i.e. as being current limited at the partial pressures being measured). An additional check of raising the partial pressure of oxygen again and checking that the output of the oxygen sensor 19a, 19b, 19c becomes static (current-limited) again can be used to confirm that the oxygen sensor 19a, 19b, 19c is current limited.

Once an oxygen sensor 19a, 19b, 19c has been confirmed as being current limited, the output of the oxygen sensor 19a, 19b, 19c can be excluded from the voting logic, so that the oxygen content of the gas 5 in the rebreather 1 is controlled based only on the outputs of the oxygen sensors 19a, 19b, 19c that are identified as working correctly. Therefore, the behaviour of the rebreather 1 may return to normal, and the partial pressure of oxygen in the gas 5 in the rebreather 1 may be controlled to be substantially equal to the target set-point.

In addition, in some embodiments simple failure modes such as a sensor output reaching a significantly high (i.e. above a predetermined threshold) or significantly low (i.e. below a predetermined threshold) output may be used to trigger an alarm, e.g. a command based alarm, or the fail-safe mode discussed above.

In other embodiments, the controller may control the operation of the rebreather 1 based on the output of one or more of the oxygen sensors 19a, 19b, 19c and additional information relating to the operation of the rebreather 1 (as an alternative to, or in addition to, using the output of a different type of sensor). In these embodiments, the rebreather 1 may not comprise an additional sensor 21 as illustrated in FIG. 1.

For example, information describing or characterising the rebreather 1 or one or more components of the rebreather 1 may be stored in a memory of the rebreather 1 (or a memory of the respective component) in advance of operation of the rebreather 1. Information that may be stored in a memory of the rebreather 1 may include information relating to an installation date of an oxygen sensor 19a, 19b, 19c, and/or information relating to an expected operational lifetime of an oxygen sensor 19a, 19b, 19c, and/or time limits for durations of operation of an oxygen sensor 19a, 19b, 19c at different oxygen contents, and/or information relating to an initial maximum output of an oxygen sensor 19a, 19b, 19c. This information may be saved in the memory by a manufacturer of the rebreather 1, or by a user of the rebreather 1 when they first operate the rebreather 1. Where the information relates to an oxygen sensor, this information may be saved in a memory of the oxygen sensor, e.g. in a solid state memory.

In addition, or alternatively, the additional information may include information or data that is determined or calculated during operation of the rebreather 1. Such derived or calculated information may include a measurement history of an oxygen sensor 19a, 19b, 19c, and/or a duration of operation of an oxygen sensor 19a, 19b, 19c, and/or durations of operation of an oxygen sensor 19a, 19b, 19c at different oxygen contents. In other words, the derived or calculated information may be information relating to the past operation of the rebreather 1, i.e. information relating to an operational history of the rebreather 1.

These types of information may be used together with the outputs of the oxygen sensors 19a, 19b, 19c to determine how to control the operation of the rebreather 1.

For example, in one embodiment the installation dates of each of the oxygen sensors 19a, 19b, 19c may be stored in a memory of the rebreather 1. The rebreather 1 may also have a clock or other time keeping means in order to determine how long each of the oxygen sensors 19a, 19b, 19c has been installed in the rebreather 1. This information may be used when controlling the operation of the rebreather 1. For example, in a voting logic more weight may be given to an output of an oxygen sensor 19a, 19b, 19c that has been more recently installed than to an oxygen sensor 19a, 19b, 19c that was installed a longer time ago.

In addition, or alternatively, a manufacturer of an oxygen sensor 19a, 19b, 19c may determine in advance how many hours the oxygen sensor 19a, 19b, 19c is able to function correctly for at different oxygen contents (e.g. different partial pressures of oxygen). For example, the manufacturer may determine that the oxygen sensor will work correctly for X hours at an oxygen content of Y, but will only work correctly for 0.5X hours at an oxygen content of 2Y. This information may be saved in a memory of the rebreather 1, for example in a solid state memory of the oxygen sensor 19a, 19b, 19c itself. For example, this information may be stored in the memory in a form of a list or table of values for time of operation and values of oxygen contents, or may be stored as a value(s) of oxygen content multiplied by allowable hours of operation (e.g. $PPO_2$ hours).

During operation of the rebreather 1, the controller may record information indicative of the number of hours that the oxygen sensors 19a, 19b, 19c have been exposed to different oxygen contents. Based on this information and on the saved information in the memory, the controller may determine whether the oxygen sensor 19a, 19b, 19c should be expected to be working correctly or not. If it is determined that an oxygen sensor 19a, 19b, 19c has been exposed to too much oxygen content (for example it has exceeded a maximum allowable value of the sum of oxygen content multiplied by hours of exposure, e.g. it has exceeded a maximum allowable value for the sum of "PPO2 hours"), it may be determined to disregard the output of that oxygen sensor 19a, 19b, 19c when controlling the operation of the rebreather 1.

For example, in the example discussed above in which two of the three oxygen sensors 19a, 19b, 19c are current-limited, and where using known voting logic the operation of the rebreather 1 would be incorrectly controlled based on the outputs of the two current-limited oxygen sensors, this may be prevented by using the additional information. For example, the additional information may indicate that the two-current limited oxygen sensors 19a, 19b, 19c were installed a long time ago, or have been exposed to high oxygen contents for a long period of time, or had a low initial maximum output, or some other information that indicates that the output of the two-current limited oxygen sensors may not be reliable. In such a case, the operation of the rebreather 1 may be controlled accordingly. For example, a user of the rebreather 1 may be alerted to the problem, for example with a visual or audible alarm or indication. In addition, or alternatively, the rebreather 1 may automatically enter a safe mode in which the operation of the rebreather 1 is controlled in a predetermined manner, e.g. in which a predetermined amount of oxygen is added to the gas 5 in the rebreather 1. Alternatively, or in addition, the controller may instigate an oxygen sensor test, for example as discussed above, to test the oxygen sensors to determine which of the oxygen sensors is working correctly. For example, this may comprise reducing the oxygen content in the gas 5 in the rebreather 1 and monitoring the outputs of the oxygen sensors 19a, 19b, 19c to identify if any of the oxygen sensors 19a, 19b, 19c is current-limited (as discussed above).

Of course, in other embodiments other types of stored and/or derived data and/or information may be used instead of the examples discussed above. The output of a different type of sensor may also be used in addition to this information. The different type of sensor may be a different type to that discussed above in relation to FIG. 1, and may be differently positioned in the rebreather 1.

Other embodiments may relate to types of breathing apparatus other than a rebreather and/or to types of breathing apparatus for specific environments, e.g. a breathing apparatus or rebreather for underwater use, or a breathing apparatus or rebreather for use in a gas environment.

The invention claimed is:

1. A controller for controlling a breathing apparatus that comprises a plurality of oxygen sensors, each for sensing an oxygen content of a gas in the breathing apparatus, the controller being configured to control the operation of the breathing apparatus based on the output of one or more of the oxygen sensors and additional information relating to the operation of the breathing apparatus;

wherein the additional information comprises information relating to an oxygen sensor of the plurality of oxygen sensors stored in a memory of the breathing apparatus;

wherein the controller is configured to identify an oxygen sensor of the plurality of oxygen sensors as not functioning correctly based on the outputs of the plurality of oxygen sensors, using an electronic voting logic system that determines how to combine the outputs of the plurality of oxygen sensors to control the oxygen content of the gas in the breathing apparatus, wherein the electronic voting logic system uses predetermined criteria to determine which oxygen sensor outputs should be used for controlling the oxygen content of the gas in the breathing apparatus, and which, if any, should be disregarded; and wherein the additional information is used to verify or check the identification of the oxygen sensor as not functioning correctly by the controller using the electronic voting logic system.

2. The controller according to claim 1, wherein the information is stored in the memory of the breathing apparatus in advance of operation of the breathing apparatus.

3. The controller according to claim 1, wherein the information comprises:
   information relating to an installation date of the oxygen sensor; and/or
   information relating to an expected operational lifetime of the oxygen sensor; and/or
   time limits for durations of operation of the oxygen sensor at different oxygen contents; and/or
   information relating to an initial maximum output of the oxygen sensor; and/or
   a manufacturing date of the oxygen sensor; and/or
   identification information for uniquely identifying the oxygen sensor.

4. The controller according to claim 1, wherein the information comprises information derived during operation of the breathing apparatus.

5. The controller according to claim 1, wherein the information comprises:
   a measurement history of the oxygen sensor; and/or
   a duration of operation of the oxygen sensor; and/or
   durations of operation of the oxygen sensor at different oxygen contents.

6. The controller according to claim 1, wherein the controller is configured to control the oxygen content of the gas in the breathing apparatus based on the output of one or more of the oxygen sensors and on the additional information relating to the operation of the breathing apparatus.

7. The controller according to claim 1, where the controller identifies an oxygen sensor of the plurality of oxygen sensors as not functioning correctly based on the output of one or more of the oxygen sensors, the controller is configured to instigate an oxygen sensor test for determining if any of the plurality of oxygen sensors is not functioning correctly.

8. The controller according to claim 1, wherein the controller is configured to:
   control the breathing apparatus to lower the oxygen content of the gas in the breathing apparatus; and
   identify an oxygen sensor of the plurality of oxygen sensors as not functioning correctly where the output of the oxygen sensor is substantially the same for a range of different oxygen contents of the gas in the breathing apparatus.

9. The controller according to claim 8, wherein the controller is further configured to:
   subsequently control the breathing apparatus to raise the oxygen content of the gas in the breathing apparatus; and
   confirm that the identified oxygen sensor is not functioning correctly where the output of the oxygen sensor is substantially the same for a range of different oxygen contents of the gas in the breathing apparatus.

10. The controller according to claim 7, wherein the controller is configured to control the oxygen content of the gas in the breathing apparatus based on the outputs of the plurality of oxygen sensors, excluding the output of any oxygen sensor identified as not functioning correctly.

11. The controller according to claim 1, wherein the controller is configured to determine whether or not an oxygen sensor of the plurality of oxygen sensors is compatible with the breathing apparatus based on identification information obtained from a memory of the oxygen sensor.

12. The controller according to claim 1, wherein the controller is configured to perform a calibration of an oxygen sensor of the plurality of oxygen sensors, and to record information about the calibration in a memory of the oxygen sensor.

13. The controller according to claim 12, wherein the information about the calibration comprises one or more of a date of the calibration, a time of the calibration, and a result of the calibration.

14. The controller according to claim 1, in which the controller is configured to identify an oxygen sensor of the plurality of oxygen sensors that is not functioning correctly, wherein where the controller identifies an oxygen sensor that is not functioning correctly the controller is configured to record in a memory of that oxygen sensor information indicating that the oxygen sensor is not functioning correctly.

15. A breathing apparatus comprising:
   a plurality of oxygen sensors, each for sensing an oxygen content of a gas in the breathing apparatus; and
   a controller according to claim 1 arranged to control the breathing apparatus.

16. The breathing apparatus according to claim 15, wherein the breathing apparatus is a rebreather.

17. A method of controlling a breathing apparatus that comprises a plurality of oxygen sensors, each for sensing an oxygen content of a gas in the breathing apparatus, the method comprising:
   controlling the operation of the breathing apparatus using a controller based on the output of one or more of the oxygen sensors and additional information relating to the operation of the breathing apparatus;
   wherein the additional information comprises information relating to an oxygen sensor of the plurality of oxygen sensors stored in a memory of the breathing apparatus;
   wherein the method comprises identifying an oxygen sensor of the plurality of oxygen sensors as not functioning correctly by the controller based on the outputs of the plurality of oxygen sensors, using an electronic voting logic system that determines how to combine the outputs of the plurality of oxygen sensors to control the oxygen content of the gas in the breathing apparatus, wherein the electronic voting logic system uses predetermined criteria to determine which oxygen sensor outputs should be used for controlling the oxygen content of the gas in the breathing apparatus, and which, if any, should be disregarded; and
   wherein the additional information is used to verify or check the identification of the oxygen sensor as not functioning correctly by the controller using the electronic voting logic system.

* * * * *